US008987494B2

(12) United States Patent
Larson et al.

(10) Patent No.: US 8,987,494 B2
(45) Date of Patent: Mar. 24, 2015

(54) LOW MOLECULAR WEIGHT CARBOSILANES, PRECURSORS THEREOF, AND METHODS OF PREPARATION

(71) Applicant: Gelest Technologies, Inc., Morrisville, PA (US)

(72) Inventors: Gerald L. Larson, Newtown, PA (US); Youlin Pan, Langhorne, PA (US); Barry C. Arkles, Pipersville, PA (US)

(73) Assignee: Gelest Technologies, Inc., Morrisville, PA (US)

( * ) Notice: Subject to any disclaimer, the term of this patent is extended or adjusted under 35 U.S.C. 154(b) by 141 days.

(21) Appl. No.: 13/777,704

(22) Filed: Feb. 26, 2013

(65) Prior Publication Data

US 2013/0274497 A1    Oct. 17, 2013

Related U.S. Application Data

(60) Provisional application No. 61/622,831, filed on Apr. 11, 2012.

(51) Int. Cl.
*C07F 7/04* (2006.01)
*C07F 7/18* (2006.01)
*C07F 7/08* (2006.01)

(52) U.S. Cl.
CPC ............. *C07F 7/1868* (2013.01); *C07F 7/0809* (2013.01); *C07F 7/083* (2013.01); *C07F 7/0867* (2013.01); *C07F 7/1836* (2013.01)
USPC ........................................................ 556/435

(58) Field of Classification Search
CPC .................................................... C07F 7/1868
USPC ........................................................ 556/435
See application file for complete search history.

(56) References Cited

U.S. PATENT DOCUMENTS

| 5,929,269 | A  | * | 7/1999  | Steding ........................ 556/479 |
| 2002/0068793 | A1 | * | 6/2002  | Mager et al. .................. 524/858 |
| 2009/0294726 | A1 | * | 12/2009 | Hamada et al. ........... 252/182.12 |
| 2012/0088193 | A1 |   | 4/2012  | Weidman et al. |
| 2012/0122302 | A1 |   | 5/2012  | Weidman et al. |

FOREIGN PATENT DOCUMENTS

| JP | 07-206418 | A  | 8/1995 |
| WO | 9510638   | A1 | 4/1995 |
| WO | 2012048108 | A2 | 4/2012 |
| WO | 2012061593 | A2 | 5/2012 |

OTHER PUBLICATIONS

Schmidbaur et al., Z. Naturforschung, Teil B: Anorg Chemie, Organ Chemie (1986), 41B(12), 1527-34.*
Fritz et al., Z. anorg. allg. Chem. 512 (1984) 93-102.*
Brondani et al, "A new trialkoxysilylation reaction, the cross-coupling of (tri-isopropyloxysilyl)methyl grignard reagent with organic halides", Journal of Organometallic Chemistry, vol. 451, pp. C1-C3 (1993).
Tamao et al, "(Diisopropoxymethylsilyl)methyl Grignard Reagent: A New, Practically Useful Nucleophilic Hydroxymethylating Agent", Journal of Organic Chemistry, vol. 48, pp. 2120-2122 (1983).
Boo et al, "Epitaxial growth of cubic SiC thin films on silicaon using single molecular precursors by metalorganic chemical vapor deposition", Journal of Vacuum Science and Technology A, vol. 19, No. 4, pp. 1887-1893 (Jul./Aug. 2001).
Jee et al, "In-situ study on thermal decomposition of 1,3-disilabutane to silicon carbide on Si(1 0 0) surface", Applied Surface Science, vol. 258, pp. 2201-2205 (2012).
Fritz, "Formation of organosilicon compounds. XXXVIII. Reaction of perchlorinated carbosilanes with lithium aluminum hydride", Zeitschrift fuer Anorganische und Allgemeine Chemie, vol. 382, No. 1, pp. 9-26 (1971) (abstract only).
Lee et al, "Trisilaalkanes; new precursors for ultrafine beta-silicon carbide powders", Bulletin of the Korean Chemical Society, vol. 14, No. 1, pp. 5-9 (1993) (abstract only).
Kovacs et al, "Formation of organosilicon compounds. 109. Reactions of perhydrogenated carbosilanes with alkyllithium compounds", Zeitschrift fuer Anorganische und Allgemeine Chemie, vol. 619, No. 9, pp. 1491-1493 (1993) (abstract only).
Fritz, "Cleavage of silicon-carbon bonds in silicon-methylated carbosilanes", Zeitschrift fuer Anorganische und Allgemeine Chemie, vol. 556, pp. 23-56 (1988) (abstract only).
Fritz et al, "Formation of organosilicon compounds. 99. Separation of carbosilane and silylphosphine mixtures using of HPLC", Zeitschrift fuer Anorganische und Allgemeine Chemie, vol. 512, pp. 93-102 (1984) (abstract only).
Fritz et al, "Formation of organosilicon compounds. 102. Reaction of chloromethanes with elemental silicon. (Formation and study of linear carbosilanes)", Zeitschrift fuer Anorganische und Allgemeine Chemie, vol. 512, pp. 131-163 (1984) (abstract only).

* cited by examiner

*Primary Examiner* — Porfirio Nazario Gonzalez
*Assistant Examiner* — Kofi Adzamli
(74) *Attorney, Agent, or Firm* — Panitch Schwarze Belisar & Nadel LLP

(57) ABSTRACT

A series of silicon compounds are provided, which are excellent precursors to small carbosilanes, such as 1,3,5-trisilapentane, 2,4,6-trisilaheptane, tris(silylmethyl)silane and tetrakis(silylmethyl)silane. A method of preparing a carbosilane involves forming a Grignard, lithium, or metallic reagent from a halomethyltrialkoxysilane, reacting the Grignard, lithium, or metallic reagent with a dihalodihydridosilane, a trihalohydridosilane, a tetrahalosilane, a dialkoxydihydridosilane, a trialkoxyhydridosilane, or a tetraalkoxysilane to yield a carbosilane precursor, and reducing the precursor to form the carbosilane.

12 Claims, No Drawings

LOW MOLECULAR WEIGHT CARBOSILANES, PRECURSORS THEREOF, AND METHODS OF PREPARATION

CROSS-REFERENCE TO RELATED APPLICATION

This application claim priority to U.S. Provisional Patent Application No. 61/622,831, filed Apr. 11, 2012, the disclosure of which is herein incorporated by reference.

BACKGROUND OF THE INVENTION

Small, volatile carbosilanes containing only carbon, hydrogen and silicon with a carbon to silicon ratio of between 2:1 and 1:2 have been shown to be excellent precursors for the deposition of silicon carbide films in microelectronic applications. Typically, the term "small carbosilane" refers to compounds containing up to about nine backbone (silicon and/or carbon) atoms. Conventional syntheses of these low molecular weight (up to about 300 Daltons) carbosilanes include 'in-situ' Grignard approaches, which invariably result in the production of a vast mixture of products, including polymeric materials. It has proven very difficult to isolate pure materials from these reaction mixtures in any useful quantities. Another conventional approach to small carbosilanes involves generating silylenes in the presence of compounds containing silicon-hydrogen bonds to effect the insertion of the silylene into the Si—H bond. However, this method, upon reduction, also yields a mixture of products, including 1,1,1,3,3,3-disilapropane as a major product. Accordingly, superior methods for preparing small carbosilanes in useful quantities would be desirable.

BRIEF SUMMARY OF THE INVENTION

The invention is directed to a novel series of silicon compounds which may be used as precursors to low molecular weight compounds containing only carbon, hydrogen, and silicon. The invention is also directed to such small carbosilanes, which have favorable C:Si ratios and would be useful as precursors for the deposition of silicon carbide thin layers.

A carbosilane precursor compound according to the invention has formula (I):

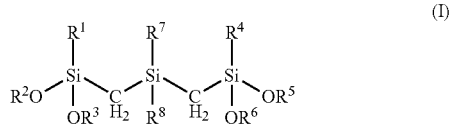

wherein $R^1$ and $R^4$ are independently selected from the group consisting of hydrogen, linear alkyl groups having one to about four carbon atoms, and linear or branched alkoxy groups having one to about eight carbon atoms, $R^2$, $R^3$, $R^5$, and $R^6$ are each independently selected from the group consisting of branched alkyl groups having about three to about eight carbon atoms, and $R^7$ and $R^8$ are independently selected from the group consisting of hydrogen, chlorine, bromine, iodine, linear and branched alkoxy groups having one to about four carbon atoms, and linear and branched alkyl groups having one to about eight carbon atoms with hydrogen, methyl, methoxy, and ethoxy being preferred.

A method of preparing a carbosilane comprises forming a Grignard, lithium, or metallic reagent from a halomethyltrialkoxysilane, reacting the Grignard, lithium, or metallic reagent with a dihalodihydridosilane, a trihalohydridosilane, a tetrahalosilane, a dialkoxydihydridosilane, a trialkoxyhydridosilane, or a tetraalkoxysilane to yield a carbosilane precursor, and reducing the precursor to form the carbosilane.

A carbosilane compound according to one embodiment of the invention has formula (IX):

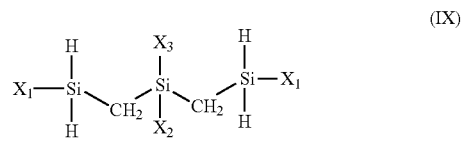

wherein $X_1$, $X_2$ and $X_3$ are each independently selected from the group consisting of hydrogen, methyl, and $CH_2SiR$, wherein R is $H_3$ or $H_2CH_3$, provided that $X_1$, $X_2$, and $X_3$ are not all hydrogen or all methyl.

A carbosilane according to a second embodiment of the invention has formula (XIII):

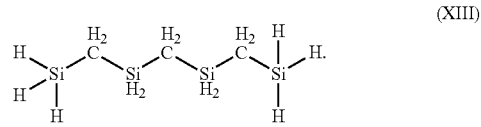

DETAILED DESCRIPTION OF THE INVENTION

The precursor silicon compounds according to the invention are shown generally in formula (I), in which $R^1$ and $R^4$ (representing the substituents on the terminal silicon atoms) are each independently hydrogen, a linear alkyl group containing one to about four carbon atoms, preferably one carbon atom, or a linear or branched alkoxy group having one to about eight carbon atoms, for example methoxy, ethoxy, isopropoxy, isobutoxy, tert-butoxy, and sterically hindered (branched) alkoxy groups such as cyclopentyl, cyclohexyl, and 2-ethylhexyl alkoxy groups; methoxy, ethoxy, isobutoxy, and isopropoxy groups are preferred alkoxy substituents. $R^2$, $R^3$, $R^5$, and $R^6$ are each independently a branched alkyl group having about three to about eight carbon atoms, including, for example isopropyl, isobutyl, tert-butyl, cyclopentyl, cyclohexyl, and 2-ethylhexyl groups. $R^7$ and $R^8$, representing the substituents on the internal silicon atoms, are each independently selected from hydrogen, chlorine, bromine, iodine, linear and branched alkoxy groups having one to about eight carbon atoms (such as methoxy, ethoxy, isopropoxy, and tert-butoxy groups), and substituted and unsubstituted linear and branched alkyl groups having one to about eight carbon atoms. Preferably, $R^7$ and $R^8$ are each independently selected from hydrogen, methyl, methoxy, and ethoxy groups.

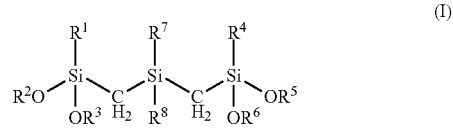

For the purposes of this disclosure, the term "about," when used to refer to a number of carbon atoms, may be understood to encompass values within one whole number from the recited value. That is, a group described as having "about four carbon atoms" would encompass three, four, and five carbon atom groups.

In a preferred group of silicon compounds according to the invention, $R^7$ is a substituted methyl group such as an alkyldialkoxysilylmethyl group or a trialkoxysilylmethyl group. Thus, $R^7$ may be represented by the formula $CH_2Si(R^{11})(OR^9)(OR^{12})$. Silicon compounds having such an $R^7$ substituent are shown generally in formula (II).

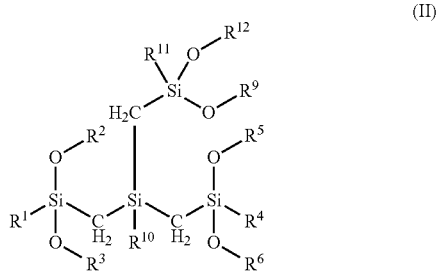

(II)

In formula (II), $R^1$ to $R^6$ are as previously defined, $R^9$ and $R^{12}$ are each independently a branched alkyl group having about three to about eight carbon atoms, such as, for example, isopropyl, isobutyl, tert-butyl, cyclopentyl, cyclohexyl, and 2-ethylhexyl groups. $R^{10}$ is selected from hydrogen, chlorine, bromine, iodine, alkoxy groups having about one to about eight carbon atoms (such as, but not limited to, methoxy, ethoxy, isopropoxy, tert-butoxy, cyclopentoxy, cyclohexoxy, and 2-ethylhexoxy groups), and linear and branched alkyl groups having about one to about eight carbon atoms. Preferably, $R^{10}$ is selected from hydrogen, methyl, methoxy and ethoxy. Finally, $R^{11}$ is a linear alkyl group containing one to about four carbon atoms, preferably one carbon atom, or a linear or branched alkoxy group having one to about eight carbon atoms, such as, for example, methoxy, ethoxy, isopropoxy, isobutoxy, tert-butoxy, and longer, sterically hindered (branched) alkoxy groups, such as cyclopentyl, cyclohexyl, and 2-ethylhexyl alkoxy groups; methoxy, ethoxy, isobutoxy, and isopropoxy are preferred alkoxy substituents.

In a second preferred group of silicon compounds according to the invention, both $R^7$ and $R^8$ are substituted methyl groups, such that each of $R^7$ and $R^8$ is an alkyldialkoxysilylmethyl group or a trialkoxysilylmethyl group. Such groups may be represented by the formulas $CH_2Si(R^{11})(OR^9)(OR^{12})$ or $CH_2Si(R^{13})(OR^{14})(OR^{15})$. Groups of silicon compounds having such $R^7$ and $R^8$ substituents may be generally shown in formula (III).

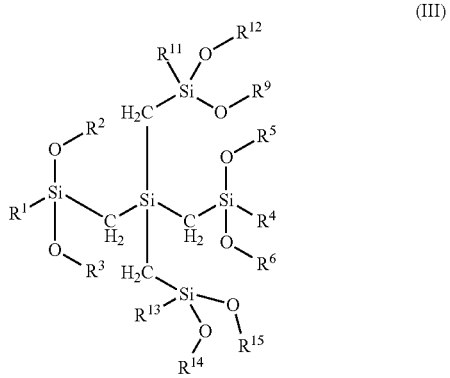

(III)

In formula (III), $R^1$ to $R^6$, $R^9$, $R^{11}$, and $R^{12}$ are as previously defined, $R^{14}$ and $R^{15}$ are each independently a branched alkyl group having about three to about eight carbon atoms, such as, for example, isopropyl, isobutyl, tert-butyl, cyclopentyl, cyclohexyl, and 2-ethylhexyl groups. $R^{13}$ is a linear alkyl group containing one to about four carbon atoms, preferably one carbon atom, or a linear or branched alkoxy group having one to about eight carbon atoms, such as, for example, methoxy, ethoxy, isopropoxy, isobutoxy, tert-butoxy, and longer, sterically hindered (branched) alkoxy groups, such as cyclopentyl, cyclohexyl, and 2-ethylhexyl groups alkoxy groups; methoxy, ethoxy, isobutoxy, and isopropoxy groups are preferred alkoxy substituents. Another potential route to structures of this general type would be through the reaction of bis(chloromagnesiomethyl)diisopropoxysilane or of bis(chloromagnesiomethyl)di-tert-butoxysilane, with the appropriate chlorosilanes. However, this route is currently considered to be less desirable due to the lack of availability of the requisite starting materials. It is further within the scope of the invention to utilize a suitably sterically hindered trialkoxysilylmethylmagnesium halide, such as triisopropoxysilylmethylmagnesium chloride, which could be reacted with bis(trichlorosilyl)methane and the resulting product reduced to 1,3,5,7-tetrasilaheptane.

It is also within the scope of the invention to prepare carbosilane precursor compounds having longer silicon-carbon backbones than those exemplified above which contain a five atom backbone. Specifically, similar compounds having backbones containing up to about nine atoms are also within the scope of the invention.

The carbosilane precursor compounds according to the invention may be synthesized via a Grignard reagent, lithium reagent, zinc reagent, or other suitable metallic reagent, preferably a Grignard reagent, which is prepared from an appropriate halomethyltrialkoxysilane in which the trialkoxysilyl group is inert to a Grignard, lithium or metallic reagent. That is, the trialkoxysilyl group does not react with the Grignard, lithium, or metallic reagent that is formed. Methods for forming Grignard, lithium, and metallic reagents are well known in the art and need not be described. The prepared Grignard, lithium, or metallic reagent is then reacted with an appropriate dihalodihydridosilane, trihalohydridosilane, tetrahalosilane, dialkoxydihydridosilane, trialkoxyhydridosilane, or tetraalkoxysilane (preferred alkoxy groups are methoxy and ethoxy) in an appropriate solvent to yield the desired product. Appropriate reaction conditions for these reactions may be determined by routine experimentation. For example, chloromethyltriisopropoxysilane may be reacted with magnesium in an ethereal solvent to form the corresponding Grignard reagent, which is then reacted with dichlorosilane to form 1,1,1,5,5,5-hexaisopropoxy-1,3,5-trisilapentane. This compound has formula (I), in which $R^1=R^4$=isopropoxy, $R^2=R^3=R^5=R^6$=isopropyl, and $R^7=R^8$=hydrogen.

The silicon compounds having formulas (I), (II) and (III) may be reduced at silicon to yield the corresponding carbosilane compounds containing only carbon, silicon, and hydrogen atoms. Reduction is preferred performed using lithium aluminum hydride ($LiAlH_4$) as a reducing agent as it provides excellent conversions. However, it is also within the scope of the invention to utilize other reducing agents which are known in the art or to be developed, including sodium aluminum hydride ($NaAlH_4$), Vitride® (sodium dihydrobis(2-methoxyethoxide) aluminate), and diisobutylalane. The reduction is preferably performed in a solvent such as diethyl ether, tetrahydrofuran, methyltetrahydrofuran, or di-n-butyl ether. Appropriate reaction conditions for the reduction may be determined by routine experimentation.

Silicon compounds having formulas (I), (II), and (III) thus represent valuable precursors to small, low molecular weight carbosilane compounds. Carbosilane compounds according to one embodiment of the invention may be generally represented by formula (IX):

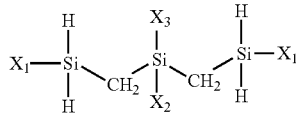

In formula (IX), $X_1$, $X_2$ and $X_3$ are each independently selected from the group consisting of hydrogen, methyl, and $CH_2SiR$, in which R may be $H_3$ or $H_2CH_3$. In preferred embodiments, $X_1$, $X_2$, and $X_3$ are not all hydrogen or all methyl. These oligomeric, volatile carbosilanes containing only silicon, carbon, and hydrogen are potential valuable precursors to silicon carbon thin layers.

Specific carbosilane compounds according to the invention include 1,3,5-trisilapentane (formula (IV)), 2,4,6-trisilaheptane (formula (V)), tris(silylmethyl)silane (formula (VI)), tetrakis(silylmethyl)silane (formula (VII)), tris(silylmethyl)methylsilane (formula (VIII)), tris(2-silapropyl)silane (formula (X)), tris(2-silapropyl)methylsilane (formula (XI)), and 5,5-bis(silylmethyl)-1,3,5,7,9-pentasilanonane (formula (XII)). Preferred carbosilane compounds are perhydridocarbosilanes wherein the Si:C ratio ranges from 3:4 to 5:3.

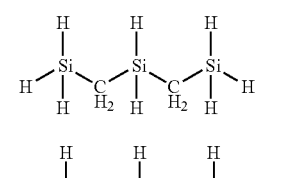

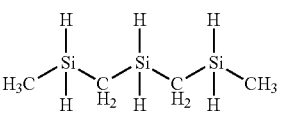

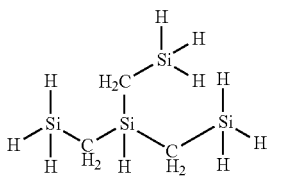

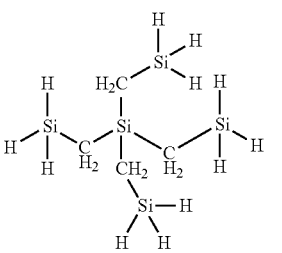

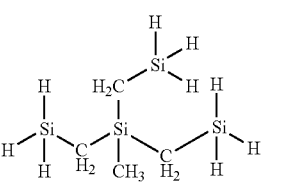

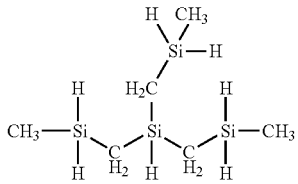

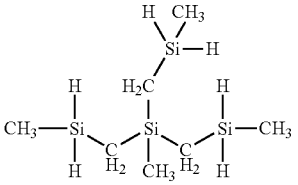

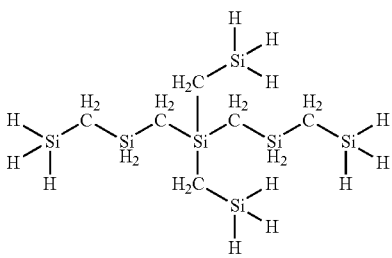

Carbosilanes according to the invention may also have a central carbon atom rather than a central silicon atom. An exemplary carbosilane of this type is 1,3,5,7-tetrasilaheptane, having formula (XIII):

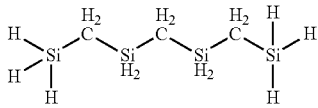

The invention will now be described in connection with the following, non-limiting examples.

Example 1

Preparation of Chloromethyltriisopropoxysilane

A 22-liter flask equipped with a condenser, addition funnel, and overhead stirring was charged with isopropanol (1.19 kg; 19.80 mol), triethylamine (2.00 kg; 19.80 mol), and hexane (4.74 kg). The resulting solution was stirred at room temperature and chloromethyltrichlorosilane (1.103 kg; 6.0 mol) was added over a 4 hour period during which time the temperature ranged from 25 to 65° C. After the addition was complete, the reaction mixture was heated at 65° C. for 2 hours and cooled to 25° C. The reaction mixture was washed with water (2×1200 mL) and the organic layer dried over sodium sulfate. Distillation of the solvent and the final product gave 1.2 kg (78% yield) of chloromethyltriisopropoxysilane, by 92-4° C./11 mm Hg; $d^{25}$ 0.957. Gas chromatographic analysis showed the product to be >99% pure.

Example 2

Preparation of
1,1,1,5,5,5-hexaisopropoxy-1,3,5-trisilapentane

A 5-liter flask equipped with a dry-ice condenser, magnetic stirring, and addition funnel was charged with magnesium (73.54 g; 3.03 mol) and tetrahydrofuran (300 mL). The magnesium was activated by the addition of a small amount of 1,2-dibromoethane. A pre-mix of chloropropyltriisopropoxysilane prepared in Example 1 (700.5 g; 2.75 mol) and tetrahydrofuran (1400 mL) was prepared and added to the flask at an appropriate rate to maintain the reaction temperature between 25 and 35° C. The addition time required 4.5 hours. After the addition was complete, the reaction mixture was stirred an additional 4 hours at 30° C. Titration showed the concentration to be 0.95 M. To this prepared Grignard reagent was added dichlorosilane in heptane (0.56 kg; 1.38 mol dichlorosilane) over a period of 1 hour, during which time the temperature rose to 50° C. After the addition was complete, the reaction mixture was stirred for an additional 6 hours at 40° C. The reaction mixture was filtered to remove the magnesium chloride salts and the salts were washed with hexane (2×110 mL). Solvent removal and distillation gave 325 g (50%) of the 1,1,1,5,5,5-hexaisopropoxy-1,3,5-trisilapentane, by 138° C./1.5 mm Hg; $d^{25}$ 0.906. Gas chromatographic analysis indicated 98% purity.

Example 3

Preparation of 1,3,5-Trisilapentane

A 5-liter flask equipped with an addition funnel, distillation column with dry-ice condenser on top, pot thermometer, and overhead stirring all under an argon atmosphere was charged with di-n-butyl ether (1.71 kg). Lithium aluminum hydride (34.2 g; 0.90 mol) was added over a 2 hour period. After the lithium aluminum hydride had fully dissolved, 1,1,1,5,5,5-hexaisopropoxy-1,3,5-trisilapentane prepared in Example 2 (210 g; 0.45 mol) was added dropwise over a period of 2 hours while maintaining the temperature below 50° C. The reaction mixture was allowed to react an additional 30 minutes at 45° C. The product, along with some solvent, was removed by distillation directly from the reaction vessel at 50° C. and 15 torr pressure. A second distillation of the product/solvent cut provided 43 g (80.7%) of 1,3,5-trisilapentane with 98.7% GC purity.

Example 4

Preparation of 3-(Silylmethyl)-1,3,5-trisilapentane

A 22-Liter flask equipped with overhead stirring, a pot thermometer, a Vigreaux column and a dry ice condenser was charged with 3.09 kg of tris(triisopropoxysilylmethyl)silane and 5 liters of di-n-octyl ether. The system was degassed under vacuum and argon bled back in a total of three times. The reaction mixture was cooled to 20° C. and 3.3 kg of diisobutylalane, DIBAL-H, was added over a 3.5 hour period. The temperature of the reaction mixture was increased to between 30 and 50° C. and a second 3.2 kg of DIBAL-H was added over a 2.5 hour period. The reaction mixture was then heated to 50° C. for another hour. The product was distilled directly from the reaction mixture to yield 550 g (74%) of 3-(silylmethyl)-1,3,5-trisilapentane having a by 60-2° C./30 mmHg, $d^{20}$ 0.806. Gas chromatographic analysis indicated 98% purity.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A carbosilane having formula (IX):

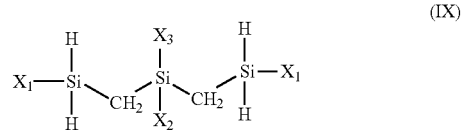

wherein $X_1$ and $X_2$ are each independently selected from the group consisting of hydrogen, methyl, and $CH_2SiR$, wherein R is $H_3$ or $H_2CH_3$, and wherein $X_3$ is $CH_2SiH_3$.

2. The carbosilane according to claim 1, wherein $X_1=X_2=CH_2SiH_3$ and the carbosilane has formula (XII):

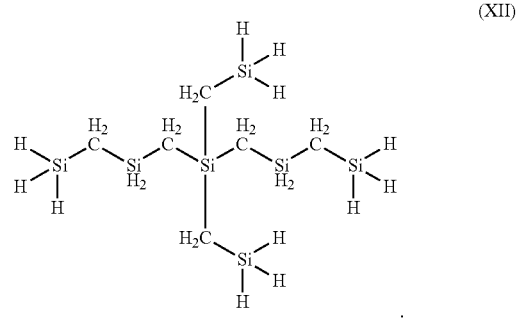

3. The carbosilane according to claim 1, wherein $X_1=X_2=H$ and the carbosilane has formula (VI):

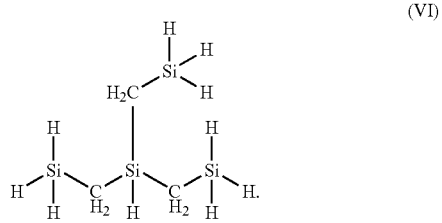

4. The carbosilane according to claim 1, wherein $X_1=H$, $X_2=CH_2SiH_3$ and the carbosilane has formula (VII):

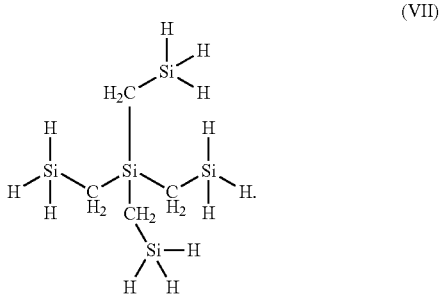

5. The carbosilane according to claim 1, wherein $X_1$=H, $X_2$=CH$_3$ and the carbosilane has formula (VIII):

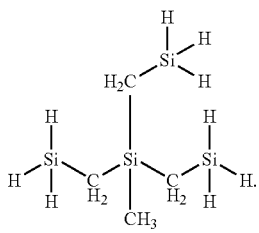

(VIII)

6. A carbosilane having formula (XI):

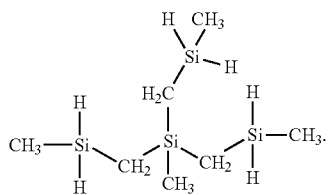

(XI)

7. A silicon compound having formula (II):

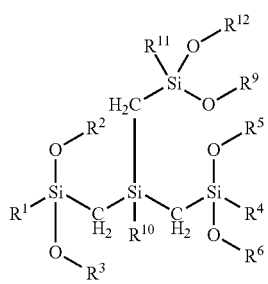

(II)

wherein $R^1$, $R^4$ and $R^{11}$ are linear or branched alkoxy groups having one to about eight carbon atoms, $R^2$, $R^3$, $R^5$, $R^6$, $R^9$, and $R^{12}$ are each independently selected from the group consisting of isopropyl, isobutyl, and tert-butyl groups, and $R^{10}$ is selected from the group consisting of hydrogen, chlorine, bromine, methoxy, and ethoxy groups.

8. The silicon compound according to claim 7, wherein $R^1$, $R^4$ and $R^{11}$ are isopropoxy groups, $R^2$, $R^3$, $R^5$, $R^6$, $R^9$, and $R^{12}$ are each independently selected from the group consisting of isopropyl, isobutyl, and tert-butyl groups, and $R^{10}$ is selected from the group consisting of hydrogen, chlorine, bromine, methoxy, and ethoxy groups.

9. The silicon compound according to claim 8, wherein $R^2$, $R^3$, $R^5$, $R^6$, $R^9$, and $R^{12}$ are isopropyl groups.

10. The silicon compound according to claim 7, wherein $R^1$, $R^4$ and $R^{11}$ are isobutoxy groups, $R^2$, $R^3$, $R^5$, $R^6$, $R^9$, and $R^{12}$ are each independently selected from the group consisting of isopropyl, isobutyl, and tert-butyl groups, and $R^{10}$ is selected from the group consisting of hydrogen, chlorine, bromine, methoxy, and ethoxy groups.

11. The silicon compound according to claim 7, wherein $R^1$, $R^4$ and $R^{11}$ are methoxy groups, $R^2$, $R^3$, $R^5$, $R^6$, $R^9$, and $R^{12}$ are each independently selected from the group consisting of isopropyl, isobutyl, and tert-butyl groups, and $R^{10}$ is selected from the group consisting of hydrogen, chlorine, bromine, methoxy, and ethoxy groups.

12. The silicon compound according to claim 7, wherein $R^1$, $R^4$ and $R^{11}$ are ethoxy groups, $R^2$, $R^3$, $R^5$, $R^6$, $R^9$, and $R^{12}$ are each independently selected from the group consisting of isopropyl, isobutyl, and tert-butyl groups, and $R^{10}$ is selected from the group consisting of hydrogen, chlorine, bromine, methoxy, and ethoxy groups.

\* \* \* \* \*